United States Patent
Hoyer

(10) Patent No.: US 11,346,847 B2
(45) Date of Patent: May 31, 2022

(54) METHOD FOR IDENTIFYING INHIBITORS OF PRIMARY NUCLEATION OF AMYLOID-BETA AGGREGATION

(71) Applicant: Forschungszentrum Juelich GmbH, Juelich (DE)

(72) Inventor: Wolfgang Hoyer, Duesseldorf (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 16/088,456

(22) PCT Filed: Apr. 6, 2017

(86) PCT No.: PCT/DE2017/000094
§ 371 (c)(1),
(2) Date: Sep. 26, 2018

(87) PCT Pub. No.: WO2017/186203
PCT Pub. Date: Nov. 2, 2017

(65) Prior Publication Data
US 2019/0317111 A1    Oct. 17, 2019

(30) Foreign Application Priority Data
Apr. 29, 2016 (DE) .................... 10 2016 005 169.8

(51) Int. Cl.
*G01N 33/68* (2006.01)
(52) U.S. Cl.
CPC . *G01N 33/6896* (2013.01); *G01N 2333/4709* (2013.01); *G01N 2800/2821* (2013.01); *G01N 2800/52* (2013.01)
(58) Field of Classification Search
CPC ....... G01N 33/6896; G01N 2800/2821; G01N 2333/4709; G01N 2800/52
See application file for complete search history.

(56) References Cited

U.S. PATENT DOCUMENTS

| | | | |
|---|---|---|---|
| 8,323,647 | B2 | 12/2012 | Ewert et al. |
| 2004/0213800 | A1 | 10/2004 | Seubert et al. |
| 2007/0021345 | A1 | 1/2007 | Gazit |
| 2010/0209422 | A1 | 8/2010 | Ravetch et al. |
| 2011/0020220 | A1 | 1/2011 | Ewert et al. |

FOREIGN PATENT DOCUMENTS

| | | |
|---|---|---|
| CN | 101463082 A | 6/2009 |
| CN | 104122400 A | 10/2014 |

OTHER PUBLICATIONS

Bergeron et al. Self-renaturing enzymes: design of an enzyme-chaperone chimera as a new approach to enzyme stabilization. Biotechnol Bioeng. Apr. 1, 2009;102(5):1316-22. doi: 10.1002/bit.22254.*
Chong et al. Protein splicing of the Saccharomyces cerevisiae VMA intein without the endonuclease motifs. J Biol Chem. Jun. 20, 1997;272(25):15587-90.*
Hortschansky et al. The aggregation kinetics of Alzheimer's β-amyloid peptide is controlled by stochastic nucleation. Protein Sci. Jul. 2005; 14(7): 1753-1759. doi: 10.1110/ps.041266605.*
Vishnu Priyanka Reddy Chichili, et al., "Linkers in the structural biology of protein-protein interactions", Protein Science, vol. 22, pp. 153-167, Dec. 2013.
Greta J. Miroy, et al., "Inhibiting transthyretin amyloid fibril formation via protein stabilization", Proc. Natl. Acad. Sci. USA, vol. 93, pp. 15051-15056, Dec. 1996.
David J. Lindberg, et al., „Steady-state and time-resolved Thioflavin-T fluorescence can report on morphological differences in amyloid fibrils formed by Aβ(1-40) and Aβ(1-42), Biochemical and Biophysical Research Communications, vol. 458, pp. 418-423, Dec. 2015.
Sejin Lee, et al., "Syntehsis of Biologically Active and Covalently Bonded Amyloid-B Dimers", (P1-118), Alzheimer's and Dementia, vol. 10, No. 4, Jul. 1, 2014, p. 344, XP055386251.
Lee Joon Seok, et al., "High-Throughput Analysis of Alzheimer's β-Amyloid Aggregation Using a Microfluidic Self-Assembly of Monomersf", Anal. Chem., vol. 81, pp. 2751-2759, Jan. 1, 2009, XP008145803.
Gunnar T. Dolphin, et al., "Designed Amyloid β Peptide Fibril-A Tool for High-Throughput Screening of Fibril Inhibitors", ChemMedChem, vol. 2, pp. 1613-1623, Nov. 1, 2007, XP002588461.
Hye Yun Kim, et al., "Synthetic β Amyloid Dimer in Anti-Parallel Conformation Induces in Vivo Synaptic Plasticity Deficits", (P4-225), Alzheimer's & Dementia, vol. 10, No. 4, Jul. 1, 2014, p. 870, XP055386252.
Johnny Habchi, et al., "An anticancer drug suppresses the primary nucleation reaction that initiates the production of the toxic Aβ42 aggregates linked with Alzheimer's disease", Sci. Adv., vol. 2, pp. 1-13, Feb. 12, 2016.
Xiaoying Chen, et al., "Fusion protein linkers: Property, design and functionality", Advanced Drug Delivery Reviews, vol. 65, pp. 1357-1369, Dec. 2013.
Paolo Arosio, et al., "Chemical kinetics for drug discovery to combat protein aggregation diseases", Trends in Pharmacological Sciences, vol. 35, No. 3, pp. 127-135, Mar. 2014.

* cited by examiner

*Primary Examiner* — Gregory S Emch
(74) *Attorney, Agent, or Firm* — Leydig, Voit & Mayer, Ltd.

(57) ABSTRACT

A method for identifying inhibitors of the primary nucleation of amyloid beta aggregation includes providing an A-beta species in solution or in a buffer, and determining the amyloid-beta aggregation, wherein the A-beta species comprises two A-beta monomer units with a linker arranged between the A-beta monomer units is provided. A method for analyzing aggregation of monomers of protein misfolding diseases and a kit are also provided.

15 Claims, 2 Drawing Sheets

Specification includes a Sequence Listing.

US 11,346,847 B2

METHOD FOR IDENTIFYING INHIBITORS OF PRIMARY NUCLEATION OF AMYLOID-BETA AGGREGATION

CROSS-REFERENCE TO PRIOR APPLICATIONS

This application is a U.S. National Phase application under 35 U.S.C. § 371 of International Application No. PCT/DE2017/000094, filed on Apr. 6, 2017, and claims benefit to German Patent Application No. DE 10 2016 005 169.8, filed on Apr. 29, 2016. The International Application was published in German on Nov. 2, 2017 as WO 2017/186203 A1 under PCT Article 21(2).

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 594 bytes ASCII (Text) file named "816640_ST25.txt," created Jan. 25, 2019.

FIELD

The invention relates to a method for identifying inhibitors of the primary nucleation of amyloid-beta aggregation.

BACKGROUND

As a result of demographic development in the coming decades, the number of people suffering from age-related illnesses will increase. These illnesses include Alzheimer's disease (AD, Alzheimer's dementia, Latin morbus Alzheimer) in particular.

Thus far, there is no active ingredient or drug that counters the causes of AD. The drugs that have been used and authorized thus far alleviate some of the symptoms that occur during Alzheimer's dementia. However, they are unable to slow the progression of the disease or to bring about healing. There are some substances that have had successes in preventing AD, but not (necessarily) in treating it, in animal studies.

One feature of Alzheimer's disease is extracellular deposits of amyloid-beta peptide (Abeta peptide, A-beta peptide, Aβ or Aβ peptide). These deposits of the A-beta peptide in plaques can typically be found in the brains of AD patients post mortem. Therefore, various forms of A-beta peptide such as fibrils are thought to be responsible for the onset and progression of the diseases. In addition, for some years the small, freely diffusible A-beta oligomers have been considered a primary originator of the onset and progression of AD.

A-beta monomers, as building blocks of A-beta oligomers, occur constantly in the human body and are presumably not toxic per se. There is even the possibility that monomers have a positive function. A-beta monomers may accumulate together by chance depending on the concentration thereof. The concentration is dependent on the formation and decomposition rates thereof in the body. If the concentration of A-beta monomers in the body increases with increasing age, spontaneous accumulation of the monomers to form A-beta oligomers becomes more and more probable. The resulting A-beta oligomers could proliferate analogously to prions and ultimately lead to Alzheimer's disease.

There are substances known in the art that reduce the concentration of A-beta monomers and/or oligomers in various ways. For example, gamma secretase modulators are known that have been used for prevention in animal testing.

Regarding many substances that have exhibited positive results in animal testing, this effect could not be confirmed in clinical studies on humans. It would be desirable to prevent the formation of the first A-beta oligomers, in other words to suppress the primary nucleation. As a result, none of the toxic oligomers would be able to form.

There is thus a need for new compounds, such as active ingredients and inhibitors, that either bind to A-beta oligomers very specifically and with a high affinity, and thus prevent the proliferation thereof, or directly inhibit the formation thereof.

Inhibitors of amyloid-beta aggregation may in principle be obtained in that molecules having a binding affinity for the amyloid-beta peptide are selected. For example, antibodies are selected by immunological methods and peptides are selected by display selection methods, and these are subsequently tested for a potential inhibitive effect on aggregation.

It is desirable to identify the inhibitors directly by way of the effect thereof on the aggregation reaction. This is possible by way of kinetic aggregation assays, as is known from Arosio et al. (Arosio, P., Vendruscolo, M., Dobson, C. M., Knowles, T. P. J. (2015). Chemical kinetics for drug discovery to combat protein aggregation diseases. Trends in Pharmacological Sciences. 35: 127-135).

Disadvantageously, however, with current kinetic aggregation assays it is only possible with great expenditure of time and materials to identify specific inhibitors of primary nucleation, as is known from Habchi et al. (Habchi, J., Arosio, P., Perni, M., Costa, A. R., Yagi-Utsumi, M., Joshi, P., Chia, S., Cohen, S. I. A., Müller, M. B. D., Linse, S., Nollen, E. A. A., Dobson, C. M., Knowles, T. P. J., Vensdruscolo, V. (2016). An anticancer drug suppresses the primary nucleation reaction that initiates the production of the toxic Ab42 aggregates linked with Alzheimer's disease. Sci. Adv. 2, e1501244: 1-13).

Thus, particularly disadvantageously, to demonstrate an inhibitive effect on primary nucleation for an individual inhibitor candidate a large number of aggregation assays have to be carried out for a plurality of A-beta concentrations and inhibitor concentrations, usually over a period of several hours, followed by complex mathematical fitting procedures.

Particularly disadvantageously, for the inhibitor candidates obtained using these methods, it remains unclear in which reaction steps of the A-beta aggregation the inhibitors actually intervene.

It is thus known that molecules are frequently selected that inhibit amyloid formation but also lead to an increased formation of potentially toxic A-beta oligomers. Molecules that specifically inhibit primary nucleation can thus only be identified in complex, tedious analyses of individual cases.

SUMMARY

In an embodiment, the present invention provides a method for identifying inhibitors of the primary nucleation of amyloid beta aggregation comprising providing an A-beta species in solution or in a buffer; and determining a level of amyloid-beta aggregation; wherein the A-beta species comprises two A-beta monomer units with a linker arranged between the A-beta monomers.

DETAILED DESCRIPTION

Figure 1:
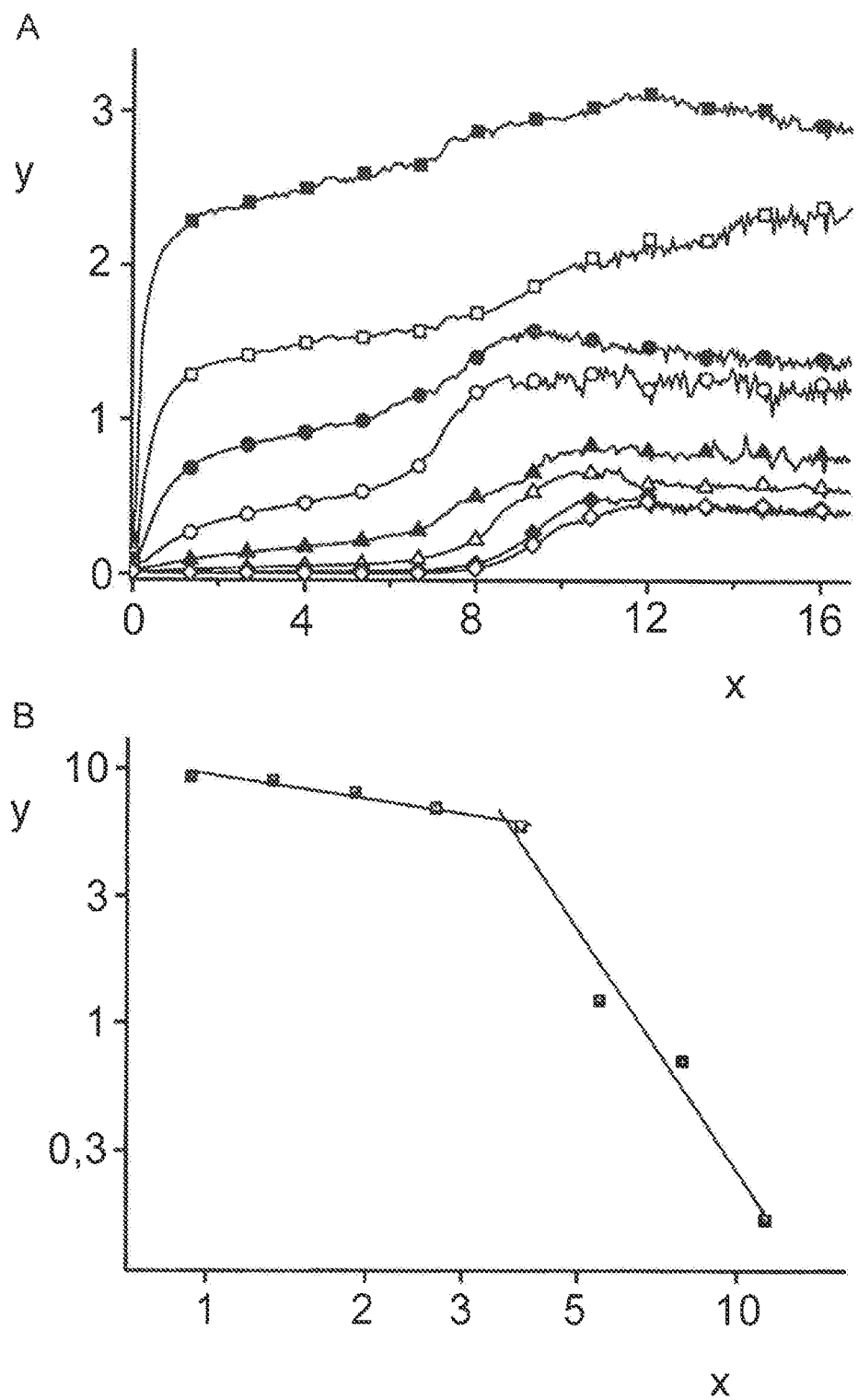
FIG. 1 shows the kinetics of the method according to certain embodiments of the invention using dimers according to certain embodiments of the invention. A: comparison between A-beta monomers, in this case A-beta (1-40) monomer and the corresponding flexidimer. B: transition between the primary nucleation and the secondary processes as a function of the concentration.

In an embodiment, the present invention provides a simpler and rapid, cost-effective method by which inhibitors of the primary nucleation of amyloid-beta aggregation can be unambiguously identified.

In another embodiment, the present invention provides suitable chemical compounds for carrying out the method and to specify the use thereof.

In another embodiment, the present invention provides a kit by means of which the method can be carried out.

According to an embodiment of the present invention, during the method for identifying inhibitors of the primary nucleation of amyloid beta aggregation, the following steps are carried out:
an A-beta species is provided in solution, in particular a buffer;
the amyloid-beta aggregation is determined.
The method is characterized in that
two A-beta monomer units with a linker arranged between the A-beta monomers are selected as the A-beta species.

In certain embodiments, the aforementioned steps are the steps carried out in a negative control for the method.

Primary nucleation refers to the occurrence of any oligomers.

In certain embodiments of the invention, the amyloid-beta aggregation and the influence of potential inhibitors can be detected in various ways, for example in multi-well plates.

For example, a fluorescent dye for detecting amyloid formation may be added to the solution or buffer. The increase in the fluorescence signal as an indicator of amyloid beta aggregation is then determined, for example by the thioflavin T test.

The following further detection methods for amyloid-beta aggregation are possible in particular:

Fluorescence spectroscopy after adding dye molecules of which the fluorescence properties (for example fluorescence intensity, fluorescence polarization) change upon binding to amyloid-beta aggregates. One example is the dye thioflavin T, which has a much higher fluorescence intensity after binding to amyloid-beta aggregates.

Fluorescence spectroscopy using A-beta flexidimer molecules that are marked with a dye and of which the fluorescence properties (for example fluorescence intensity, fluorescence polarization) change upon binding to amyloid-beta aggregates.

Dynamic light scattering as an established method for detecting (nano)particles and protein aggregates.

These measurements are taken against time.

In certain embodiments of the invention, peptide linkers between the A-beta species that are marked with dyes may be selected.

The linker has a number of advantages. It greatly reduces the lag phase of amyloid-beta aggregation, preferably by at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or even 100% by comparison with the lag phase during the aggregation of the correspondingly unlinked monomers.

Thus, in the method according to certain embodiments of the invention, the amyloid-beta aggregation starts immediately after the linked A-beta monomers are added to the buffer.

For the method, this means that, if an increase in the fluorescence signal took place after approximately 10 hours' incubation time in a method using unlinked monomers, employing a method according to certain embodiments of the invention ensures that the lag phase is concluded after 2 hours at the latest for a lag phase reduced by 80% or after 1 hour at the latest for a lag phase reduced by 90% or after an even shorter time.

It has been found that the method according to certain embodiments of the invention causes the local concentration of A-beta species to be increased by the linking of two A-beta monomers and thus makes it possible to accelerate the amyloid-beta aggregation.

It has been found that, in absolute terms, the method according to certain embodiments of the invention also requires less A-beta species material if linked A-beta monomers are used by comparison with an assay in which unlinked A-beta monomers are used in solution. The method is thus more cost-effective.

The primary advantage is the greatly reduced lag phase in which, unlike in other methods, there are no longer any secondary processes superposed on the primary nucleation. Therefore, using the method according to certain embodiments of the invention, unambiguous detection of the inhibitive effect of substances in relation to primary nucleation in amyloid-beta aggregation can be provided.

The method according to certain embodiments of the invention is thus the negative control of a method in which potential inhibitors of primary nucleation that are already known can be tested for effectiveness so as to prevent amyloid-beta aggregation.

As examples, A-beta (1-42), but also A-beta (1-40) or any other A-beta species, such as pyro-glu-A-beta (3-40, 3-42), are conceivable as A-beta species or monomers, and may be selected in accordance with the assay approach. The method is applicable to all known A-beta monomers.

It is conceivable to test not only the A-beta monomers of Alzheimer's dementia and the aggregation thereof in this way, but also the monomers of other protein misfolding diseases. In this case, the monomers of the proteins occurring in these diseases are linked to one another.

In the case of AD, it is possible but not necessary for two identical A-beta species units to be selected, which are linked, head-to-tail or otherwise, using the linker. Thus, A-beta monomers of different A-beta species may also be linked to one another, for example A-beta (1-40) to A-beta (1-42).

Head-to-tail means that the linker is arranged between the C-terminus of a first A-beta monomer unit and the N-terminus of the second A-beta monomer unit by preferably covalent peptide binding.

Preferably, a peptide linker having a flexible conformation (intrinsically disordered conformation) may be selected as a linker. So as to make a flexible conformation possible and prevent interactions between the linker and the A-beta monomer units, the linker may be rich in polar, uncharged amino acids, such as serine, threonine and/or asparagine and/or glutamine, and also rich in small amino acids, such as glycine and/or alanine and/or proline. The linker may in particular be selected to be rich in glycine and/or serine, and it may also in particular consist exclusively of glycine and serine.

In certain embodiments of the invention, the method may provide NMR spectroscopy as a further step, so as to show that the linker is not intervening in the morphology of the fibrils in the aggregated state and/or that the A-beta monomers attain the native conformation thereof in the dimer.

The linker in particular does not influence the intrinsically disordered conformation of the A-beta units in the solution or in the buffer. In particular, the linker also does not change the morphology of the amyloid fibrils in the aggregated state.

The method and the kinetics of the aggregation of A-beta units linked in this manner are substantially shaped by the primary nucleation, in particular at concentrations of A-beta species in the buffer of approximately 1-50 μM, preferably 1 μM, 2 μM, 5 μM, 10 μM, 20 μM to approximately 50 μM, this being attributable to the increase in the local concentration of A-beta. In this context, any intermediate value may be taken.

Thus, with the linker, the natural properties of the peptides are not influenced. In particular, the intrinsically disordered conformation properties prior to the conformation of the fibrils and/or aggregates are not influenced by the linker.

In certain embodiments of the invention, the method may have a step in which the conformation of the linked A-beta species is compared with that of the unlinked units, for example by NMR measurements.

The linked units serve as a model substance for the unlinked units.

In certain embodiments of the invention, he method may have a step in which there is an analysis as to the linked A-beta species forming, or as to whether they form, the same shape of fibrils as the unlinked A-beta species. For this purpose, for example atomic force microscopy may be carried out.

The method according to certain embodiments of the invention is suitable for high-throughput screening, for example in multi-well microtiter plates.

The method is carried out in particular to test the kinetics of primary nucleation. For this purpose, in certain embodiments of the invention, a microtiter-based assay may be carried out with and without inhibitors of amyloid-beta aggregation.

In particular a peptide linker having the sequence $(Gly_x\text{-}Ser_y)_n$ may be selected as a linker, where x=1-4, y=1 and n=1-10.

Threonine and/or asparagine and/or glutamine may be selected instead of the serine. These amino acids advantageously maintain the stability.

Alanine and/or proline may be selected instead of the glycine.

As a rule of thumb, approximately 10-90% as many amino acids should be present in the linker as in the linked A-beta species. In general, in the case of protein misfolding diseases, the linker should comprise approximately 10-90% of the number of amino acids of the monomer units triggering the aggregation. For A-beta (1-40), the linker comprises approximately 4-36 amino acids in this case. In particular, the linker comprises 20-80%, 30-70%, 40-60%, 20%, 30%, 40%, 50%, 60%, 70% or 80% of the amino acid number of the monomer units triggering the aggregation.

As a further rule of thumb, in particular approximately 50%±5% as many amino acids should be present in the linker as in the linked A-beta species. In general, in the case of protein misfolding diseases, the linker should have approximately 50%±5% of the number of amino acids of the monomer units triggering the aggregation.

In particular, a peptide linker having the sequence $(Gly_4\text{-}Ser)_4$ has been found to be expedient, it being possible for the above-mentioned conditions on replacement with other amino acids to be applied.

These linkers particularly can greatly reduce the lag phase of the amyloid-beta aggregation of Alzheimer's dementia, in particular but not exclusively in the case of A-beta (1-40) and/or A-beta (1-42) as A-beta species to be linked.

The concentration at which the linked A-beta species are to be provided should in particular be approximately >2 μM. In this case, the reduction in the lag phase and the dominance of the primary nucleation are particularly pronounced.

The aforementioned method and the accompanying reduction in the lag phase ensure that the amyloid-beta aggregation starts immediately and is detectable. Thus, the influence of potential active ingredient candidates on the kinetics of the primary nucleation is detectable.

Above-mentioned linkers according to certain embodiments of the invention between the A-beta species or monomer units of different protein misfolding diseases greatly reduce the lag phase of an (amyloid-beta) aggregation, preferably by at least 80%.

A substance to be tested, for example an inhibitor, is added and is positively evaluated if it either limits the level of the fluorescence signal and/or slows the increase in the fluorescence signal with respect to time by comparison with the signal of the negative control.

The flexible linker having amino acid sequence ggggsggggsggggsggggs as the peptide in accordance with SEQ ID NO: 1 is provided by way of example, and is particularly relevant because it has the required properties. This linker is used in the identification of active ingredients and inhibitors of the primary nucleation of amyloid-beta aggregation, in particular from A-beta (1-40) and/or A-beta (1-42) and/or other monomers from protein misfolding diseases, it again being intended for the above-mentioned rules for the possibility of replacement with other amino acids to be applied.

A kit for carrying out the method according to certain embodiments of the invention comprises:

A-beta species, lyophilized;

buffer or solution;

optionally a fluorescent dye for detecting amyloid formation or aggregation;

wherein the A-beta species consists of two A-beta monomer units along with a linker arranged between the A-beta monomers.

The components of the kit are dissolved in buffer or solution prior to use and are thus ready for immediate use.

The linker does not influence the β-sheet structure of the amyloid-beta aggregation.

Thus, by way of known techniques, in this case a thioflavin test, the amyloid-beta aggregation in multi-well plates can be detected by measuring the increase in the fluorescence signals over time, and the influence of the potential inhibitors can be detected.

In certain embodiments of the invention, the kit is provided without the fluorescent dye, for example if the amyloid-beta aggregation is detected in a different way, for example using light scattering or other methods, as set out above.

The substances, in particular the active ingredients or inhibitors that inhibit the A-beta aggregation, are accordingly promising active ingredient candidates for treating Alzheimer's disease, since with the method according to certain embodiments of the invention the particularly toxic oligomers do not even occur in the first place. Within this meaning, the method leads to the secondary processes of amyloid-beta aggregation being temporally skipped over.

Particularly the inhibitors of the very first steps of the aggregation reaction, known as primary nucleation, are thus also of interest as active ingredients. Inhibitors of this type potentially suppress the formation of the particularly toxic A-beta oligomers of Alzheimer's dementia.

By the method according to certain embodiments of the invention, it is possible in a particularly simple and accelerated manner to identify reliable inhibitors of the primary nucleation of amyloid-beta aggregation by way of corresponding reduction in the lag phase and thus to discover active ingredients against the formation of toxic oligomers in a cost-effective manner.

In this context, naturally the molecules already identified in the art such as peptides, antibodies, active ingredients for treating cancer, such as bexarotene, may be used in the shortened assay according to certain embodiments of the invention and be analyzed for the effectiveness thereof in suppressing the formation of toxic oligomers. In certain embodiments of the invention, these may be used as a positive control.

For this purpose, in the context of the invention, it is found that amyloid-beta aggregation is a complex reaction consisting of a plurality of steps, in which subsequent, secondary processes dominate the observable reaction progression of conventional, prior art assays. It is further found that these subsequent processes occur during the lag phase.

Accordingly, according to certain embodiments of the invention, by shortening the lag phase a kinetic aggregation assay is developed that is dominated by the primary nucleation and not by secondary processes.

Instead of monomeric A-beta, the assay and the method according to certain embodiments of the invention and the kit use a newly developed dimeric construct having the working title "A-beta flexidimer", in which two A-beta monomers are interconnected via a flexible peptide linker. For this purpose, for example two units of the most common A-beta variant, A-beta (1-40), may be used. Dimers of other A-beta variants, such as A-beta (1-42) or modified versions, including shorter versions, and mixtures thereof are of interest and therefore constitute subject matter according to certain embodiments of the invention. Merely by way of example, an A-beta (1-40) monomer may be linked to an A-beta (1-42) monomer.

The relatively high length of the linker has been selected in such a way that the A-beta units in the dimeric construct are not inhibited by the interaction with the fused neighbors in the formation of the usual amyloid structure, as can be confirmed by atomic force microscopy measurements.

By comparison with A-beta monomer, A-beta flexidimer advantageously has improved behavior in kinetic aggregation assays, in the present case in the method according to certain embodiments of the invention. It is advantageously characterized in that it almost completely eliminates the lag phase. For this purpose, the concentration in the buffer may be from 1 μM to approximately 50 μM, preferably approximately 5 μM. This advantageously results in the considerable saving on time in carrying out the test method. Moreover, in this way an added active ingredient can be identified as an active ingredient that actually inhibits the primary nucleation and does not only intervene in the further aggregation at a later time, at simultaneously reduced A-beta monomer concentrations.

These positive effects were not to be expected from publications relating to linkers, for example from Chen et al. (Chen, X., Zaro, J., Shen, W.-C. (2013). Fusion protein linkers: Property, Design and Functionality. Adv Drug Deliv Rev 65(10):1357-1369) or from Chichilli et al. (Chichilli, V. P. R., Kumar, V., Sivaram J. (2013). Protein Science 22:153-167).

In this way, the inhibitors are identified that prevent the formation of toxic oligomers and are conceivable as active ingredients against the corresponding protein misfolding diseases.

The invention is not limited hereto. Rather, certain embodiments of the invention relate to further methods that are directed to the aggregation of monomers of protein misfolding disease in general, for instance:

a method for analyzing the aggregation of monomers of protein misfolding diseases (i.e., monomer species), comprising the following steps:

the monomer of the protein misfolding disease is provided in solution or in a buffer;

the aggregation of the monomers is determined;

a. characterized in that b. two units of the monomer occurring in the protein misfolding disease with a linker arranged between the monomer units are selected as the monomer (i.e., monomer species).

The linker comprises the features as described above.

It will be appreciated that for this purpose A-beta monomers, such as the aforementioned A-beta (1-42) and/or A-beta (1-40) and/or other monomers occurring in Alzheimer's dementia can be tested for the aggregation properties thereof. Moreover, any other monomer of another protein misfolding disease can be tested in the manner according to certain embodiments of the invention in accordance with the disclosed methods, and a kit and a peptide linker for this purpose can be claimed.

EXAMPLES

Hereinafter, the invention is described in greater detail by way of embodiments and the accompanying drawings, without this resulting in the invention being limited to amyloid-beta aggregation.

Example 1

A 25 μM solution of A-beta flexidimer in a buffer, for example in 20 μM sodium phosphate, pH 7.4, 50 μM NaCl, is provided in a microtiter plate. A dye for detecting amyloid formation, for example thioflavin T, is added.

The influence of A-beta monomer flexidimer on the reduction of the lag phase is shown in FIG. 1.

The time in hours is plotted on the x-axis and the fluorescence intensity as a measure of the aggregation is plotted on the y-axis. At initial concentrations >1 μM, the aggregation of A-beta flexidimer is detectable directly from the start of the aggregation assay without a delay time (FIG. 1A, hollow diamond 0.9 μM, solid diamond 1.3 μM, hollow triangle 1.9 μM, solid triangle 2.7 μM, hollow circles 3.9 μM, solid circles 5.5 μM, hollow squares 8 μM, solid squares 11 μM).

This behavior is in accordance with a transition from dominant secondary processes to dominant primary nucleation at A-beta flexidimer concentrations >2 μM (FIG. 1B). FIG. 1B shows a double logarithmic plot of $t_{1/2}$ (in hours) against the concentration of flexidimer (in μM). Starting from a concentration of approximately 3 μM, the primary nucleation is the dominant process in the amyloid-beta aggregation of A-beta flexidimer. An increase of approximately −0.3 shows the dominance of secondary processes and an increase of approximately −3 shows the dominance of the primary nucleation.

Figure 2:
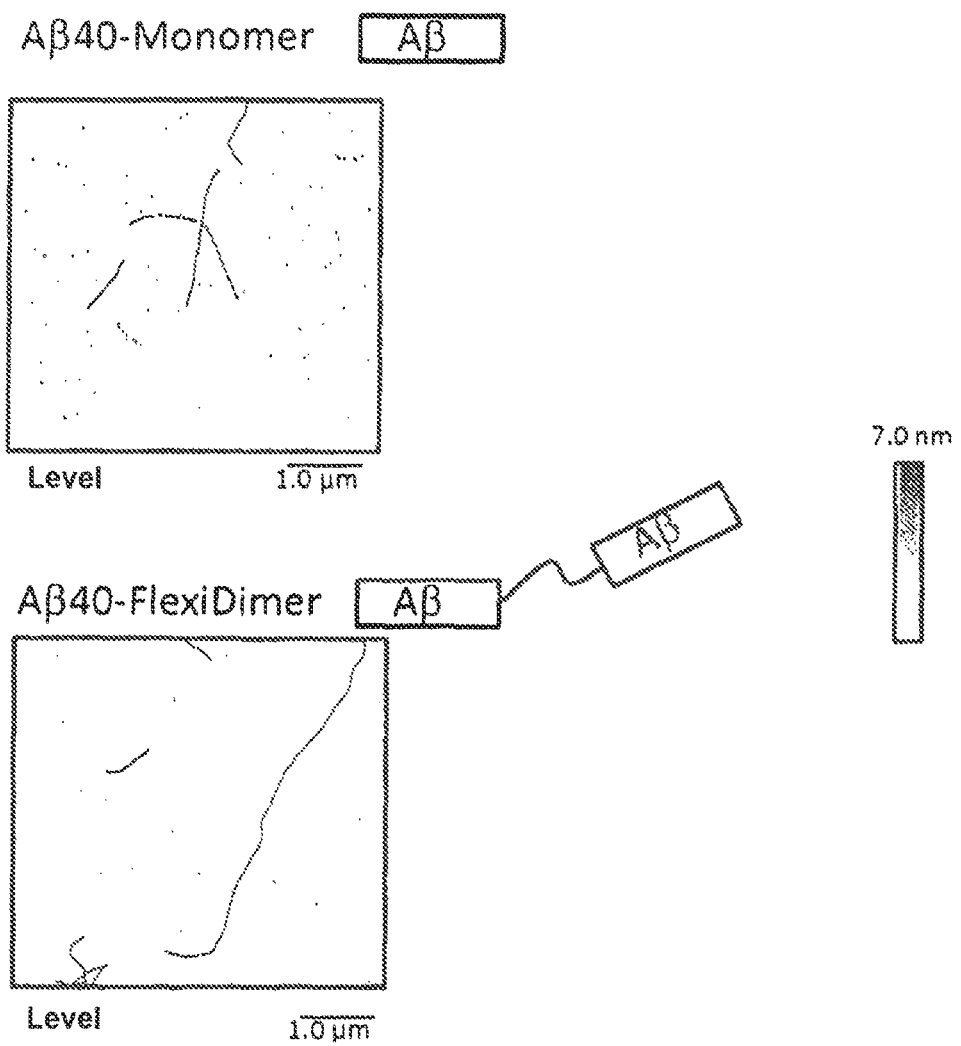
FIG. 2 is a model comparison between A-beta (1-40) amyloid formation and the fibril formation of the flexidimer.

FIG. 2 shows, by way of atomic force microscopy, that the flexidimer forms fibrils of the same morphology as the A-beta monomer, in this case for A-beta (1-40).

Inhibitor candidates are added to the individual wells. The microtiter plate is incubated in a fluorescence reader at 37° C., and the fluorescence is determined at regular intervals within a period of a few minutes.

Inhibitors are identified in that they hold back or slow down the increase in the fluorescence signal over time (not shown).

Further Examples

1. A 25 µM solution of A-beta flexidimer in a buffer, for example in 20 µM sodium phosphate, pH 7.4, 50 µM NaCl, is provided in a microtiter plate. A dye for detecting amyloid formation, for example thioflavin T, is added. The fluorescence intensity in the absence and presence of inhibitors is measured using a fluorescence reader.

2. A-beta flexidimer is marked using a suitable dye molecule that indicates amyloid-beta aggregation by way of an increase in the fluorescence polarization. A 25 µM solution of the marked A-beta flexidimer in a buffer, for example in 20 µM sodium phosphate, pH 7.4, 50 µM NaCl, is provided in a microtiter plate. The fluorescence polarization in the absence and presence of inhibitors is measured using a fluorescence reader.

3. A 25 µM solution of A-beta flexidimer in a buffer, for example in 20 µM sodium phosphate, pH 7.4, 50 µM NaCl, is provided in a microtiter plate. The light scattering in the absence and presence of inhibitors is measured using a light scattering detector.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for identifying inhibitors of the primary nucleation of amyloid beta aggregation comprising:
   providing an A-beta species in solution or in a buffer; and
   determining a level of amyloid-beta aggregation;
   adding a fluorescent dye for detecting amyloid formation to the solution or buffer;
   measuring the fluorescence signal, wherein an increase in signal indicates amyloid-beta aggregation;
   adding a candidate inhibitor to the solution or buffer; and
   determining that inhibition is present if the fluorescence signal stops increasing or increases at a slower rate;
   wherein the A-beta species comprises two A-beta monomer units (1-40), two A-beta monomer units (1-42), or one A-beta monomer unit (1-40) and one A-beta monomer unit (1-42) with a linker arranged between the A-beta monomer units, and the linker is a peptide linker with the sequence $(Gly_x-Ser_y)_n$, with x=1-4, y=1 and n=1-10, and wherein the concentration of the A-beta species in the solution or buffer is between approximately 2 µM and 50 µM; and
   wherein the A-beta species with the peptide linker arranged between the A-beta monomers reduces the lag phase of the amyloid beta aggregation by at least 50% compared to the lag phase in the aggregation of the corresponding unlinked monomers.

2. The method of claim 1, wherein the A-beta species comprises two identical A-beta monomer units.

3. The method of claim 1, wherein the linker has a flexible conformation.

4. The method of claim 1, wherein the linker has a number of amino acids corresponding to 50%±5% of the number of amino acids in the A-beta monomers.

5. The method of claim 1, wherein the linker has the sequence $(Gly_4\text{-}Ser)_4$.

6. The method of claim 1, wherein the amino acid glycine is replaced with the amino acid alanine and/or proline in the sequence of the linker.

7. The method of claim 1, wherein the amino acid serine is replaced with the amino acid threonine and/or asparagine and/or glutamine in the sequence of the linker.

8. The method of claim 1, wherein the A-beta species comprises two A-beta (1-40) monomer units.

9. The method of claim 1, wherein the A-beta species comprises two A-beta (1-42) monomer units.

10. The method of claim 1, wherein the A-beta species comprises one A-beta (1-40) monomer unit and one A-beta (1-42) monomer unit.

11. A method for analyzing aggregation of monomers of protein misfolding diseases comprising:

providing at least two units of a monomer occurring in the protein misfolding disease with a linker arranged between the monomer units of the protein misfolding disease in solution or in a buffer; and determining a level of aggregation of the monomer species, wherein the A-beta species comprises two A-beta monomer units (1-40), two A-beta monomer units (1-42), or one A-beta monomer unit (1-40) and one A-beta monomer unit (1-42) with a linker arranged between the A-beta monomer units, and the linker is a peptide linker with the sequence $(Gly_x\text{-}Ser_y)_n$, with x=1-4, y=1 and n=1-10, and wherein the concentration of the A-beta species is between approximately 2 μM and 50 μM; and wherein the A-beta species with the peptide linker arranged between the A-beta monomers reduces the lag phase of the amyloid beta aggregation by at least 50% compared to the lag phase in the aggregation of the corresponding unlinked monomers.

12. The method of claim 11, wherein the linker comprises the amino acid sequence of SEQ ID NO: 1.

13. The method of claim 11, wherein the at least two monomer units comprise two A-beta (1-42) monomer units.

14. The method of claim 11, wherein the at least two monomer units comprise two A-beta (1-40) monomer units.

15. The method of claim 11, wherein the at least two monomer units comprise one A-beta (1-40) monomer unit and one A-beta (1-42) monomer unit.

* * * * *

```
SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Peptide Linker

<400> SEQUENCE: 1

Gly Gly Gly Gly Ser Gly Gly Gly Ser Gly Gly Gly Gly Ser Gly
1               5                   10                  15

Gly Gly Gly Ser
            20
```